United States Patent
Shiomitsu (10) Patent No.: US 10,537,722 B2
(45) Date of Patent: Jan. 21, 2020

(54) MICRONEEDLE AND MICRONEEDLE ASSEMBLY

(71) Applicant: TOPPAN PRINTING CO., LTD., Taito-ku (JP)

(72) Inventor: Kazuhiko Shiomitsu, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 0 days.

(21) Appl. No.: 15/404,345

(22) Filed: Jan. 12, 2017

(65) Prior Publication Data

US 2017/0120027 A1 May 4, 2017

Related U.S. Application Data

(63) Continuation of application No. PCT/JP2015/070157, filed on Jul. 14, 2015.

(30) Foreign Application Priority Data

Jul. 15, 2014 (JP) ................................ 2014-145140

(51) Int. Cl.
*A61M 37/00* (2006.01)

(52) U.S. Cl.
CPC . *A61M 37/0015* (2013.01); *A61M 2037/0023* (2013.01); *A61M 2037/0053* (2013.01)

(58) Field of Classification Search
CPC .. A61M 2037/0023; A61M 2037/0053; A61M 37/0015; A61M 2037/0046; A61M 2025/0093

See application file for complete search history.

(56) References Cited

U.S. PATENT DOCUMENTS

| | | | | |
|---|---|---|---|---|
| 9,492,647 | B2 * | 11/2016 | Stumber | A61M 37/0015 |
| 2005/0203575 | A1 * | 9/2005 | Carson | A61M 37/0015 |
| | | | | 606/204.35 |

(Continued)

FOREIGN PATENT DOCUMENTS

| | | | |
|---|---|---|---|
| JP | 2006-341089 A | 12/2006 |
| JP | 2006-345983 A | 12/2006 |

(Continued)

OTHER PUBLICATIONS

Extended European Search Report dated Feb. 16, 2018 in Patent Application No. 15821366.0, 9 pages.

(Continued)

*Primary Examiner* — Quynh-Nhu H. Vu
(74) *Attorney, Agent, or Firm* — Oblon, McClelland, Maier & Neustadt, L.L.P.

(57) ABSTRACT

A microneedle including a substrate having a first surface and a second surface opposite to the first surface, at least one piercing projection projecting from the first surface of the substrate and being surrounded by an outer peripheral region of the substrate when viewed in a direction perpendicular to the first surface, and surface-defining structures positioned in the outer peripheral region and including three or more surface-defining structures each having a surface-defining section which is one of a surface-defining projection and a surface-defining recess. The surface-defining projection protrudes from the first surface and has a tip which serves as the surface-defining section, the surface-defining recess is recessed from the first surface and has a bottom serving as the surface-defining section, and the piercing projection has a tip that extends beyond a plane including the surface-defining sections of three surface-defining structures among the surface-defining structures.

20 Claims, 5 Drawing Sheets

(56) References Cited

U.S. PATENT DOCUMENTS

| | | | |
|---|---|---|---|
| 2007/0004989 A1* | 1/2007 | Dhillon | A61M 37/0015 600/583 |
| 2007/0293814 A1* | 12/2007 | Trautman | A61M 37/0015 604/46 |
| 2010/0305518 A1* | 12/2010 | Moga | A61M 37/0015 604/272 |
| 2015/0051582 A1* | 2/2015 | Pettis | A61M 5/28 604/506 |
| 2015/0057604 A1 | 2/2015 | Arami et al. | |

FOREIGN PATENT DOCUMENTS

| | | |
|---|---|---|
| JP | 2008-212588 A | 9/2008 |
| JP | 2009-61144 A | 3/2009 |
| JP | 2009-240410 A | 10/2009 |
| JP | 2012-55343 A | 3/2012 |
| JP | 2013-94224 A | 5/2013 |
| JP | 3185527 U | 8/2013 |
| JP | 2013-236865 A | 11/2013 |
| WO | WO 2013/151044 A1 | 10/2013 |

OTHER PUBLICATIONS

International Search Report dated Oct. 20, 2015 in PCT/JP2015/070157, filed Jul. 14, 2015.
Office Action dated Jul. 2, 2019 in corresponding Japanese Patent Application No. 2016-534445, filed Jul. 14, 2015 (with English-language Translation), 6 pages.

* cited by examiner

MICRONEEDLE AND MICRONEEDLE ASSEMBLY

CROSS-REFERENCE TO RELATED APPLICATIONS

The present application is a continuation of International Application No. PCT/JP2015/070157, filed Jul. 14, 2015, which is based upon and claims the benefits of priority to Japanese Application No. 2014-145140, filed Jul. 15, 2014. The entire contents of these applications are incorporated herein by reference.

BACKGROUND OF THE INVENTION

Field of the Invention

The present invention relates to microneedles used for drug administration and microneedle assemblies having a microneedle and an applicator.

Discussion of the Background

Drug administration using a microneedle is known as a method of administration of drugs such as vaccine into the body (for example, see PTLs 1 and 2). The microneedle includes a plurality of piercing projections having a needle-shape formed on the surface of a substrate. In the administration method using a microneedle, the substrate is pressed against the skin so that the piercing projections puncture the skin to form holes, through which a drug is delivered into the skin. Since the piercing projection has a length that does not reach nerve cells in the dermis layer of the skin, the administration method using a microneedle reduces pain caused by puncturing the skin compared with an administration method using an injection needle. Further, in the administration method using a microneedle, a drug is administered into the skin, which is abundant in antigen-presenting cells. Accordingly, the dose of the drug is reduced compared with a subcutaneous injection.

PTL 1: JP-A-2006-345983
PTL 2: JP-A-2006-341089

SUMMARY OF THE INVENTION

A microneedle including a substrate having a first surface and a second surface opposite to the first surface, at least one piercing projection projecting from the first surface of the substrate and being surrounded by an outer peripheral region of the substrate when viewed in a direction perpendicular to the first surface, and surface-defining structures positioned in the outer peripheral region and including three or more surface-defining structures each having a surface-defining section which is one of a surface-defining projection and a surface-defining recess. The surface-defining projection protrudes from the first surface and has a tip which serves as the surface-defining section, the surface-defining recess is recessed from the first surface and has a bottom serving as the surface-defining section, and the piercing projection has a tip that extends beyond a plane including the surface-defining sections of three surface-defining structures among the surface-defining structures.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

The embodiments will now be described with reference to the accompanying drawings, wherein like reference numerals designate corresponding or identical elements throughout the various drawings.

With reference to FIGS. 1 to 8, an embodiment of a microneedle and a microneedle assembly will be described.

Structure of microneedle

Figure 1:
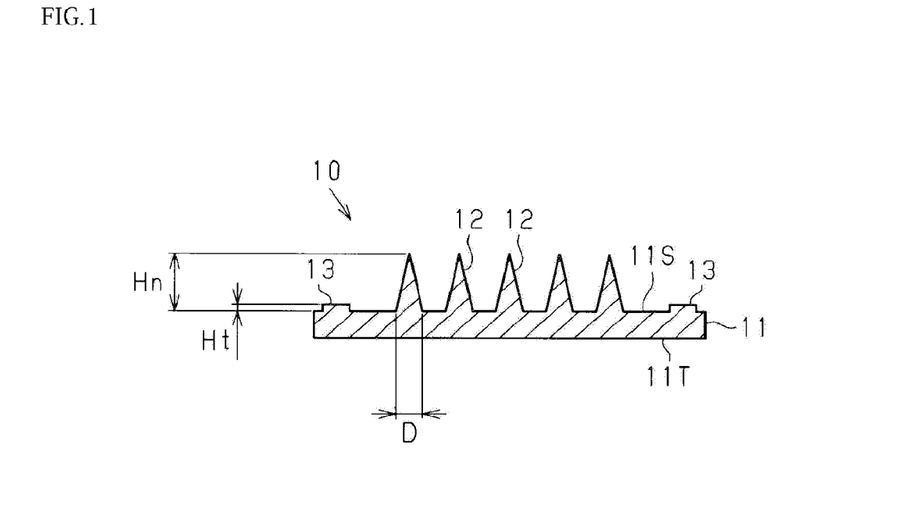
FIG. 1 is a cross sectional view which shows a cross sectional structure of a microneedle according to an embodiment.
Figure 2:
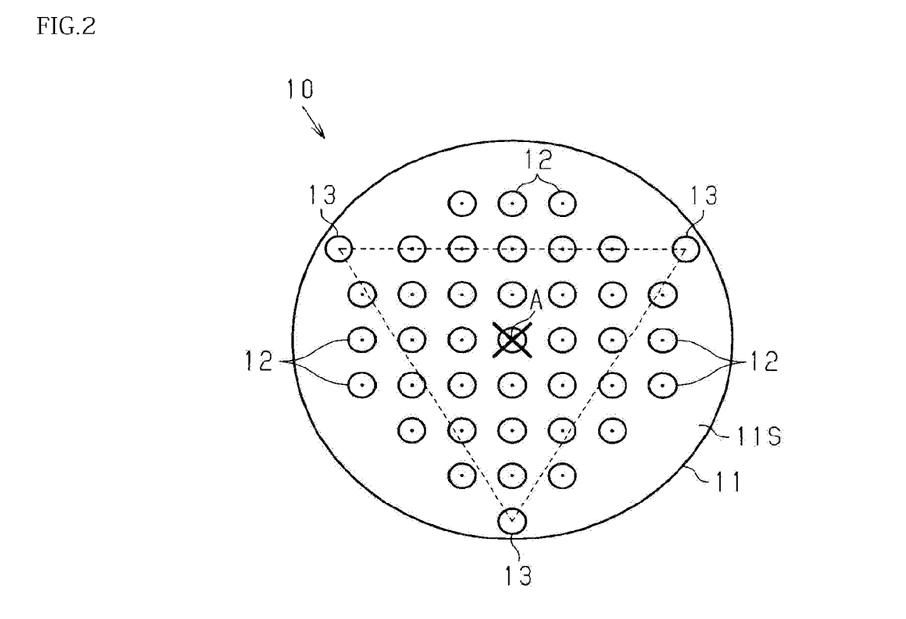
FIG. 2 is a plan view which shows a planar structure of a microneedle according to an embodiment.

With reference to FIGS. 1 and 2, a structure of a microneedle 10 will be described.

As shown in FIG. 1, the microneedle 10 includes a plate-shaped substrate 11, piercing projections 12 that protrude from the substrate 11, and non-piercing projections 13, which are examples of surface-defining projections that protrude from the substrate 11. The surface-defining projection is an example of a surface-defining structure. The substrate 11, the piercing projection 12 and the non-piercing projection 13 are formed as a unity.

The substrate 11 is formed, for example, in a disk shape, and has a first surface 11S on which the piercing projections 12 are formed and a second surface 11T which is a surface opposite from the first surface 11S. The non-piercing projections 13 are formed on the first surface 11S. The first surface 11S supports proximal ends of the piercing projections 12 and the proximal ends of the non-piercing projections 13. That is, the piercing projections 12 and the non-piercing projections 13 are formed to protrude from the substrate 11 in the same direction. Further, the first surface 11S and the second surface 11T are not necessarily flat surfaces, and may have a roughness or curvature. In other words, any configuration can be used as long as the first surface 11S constitutes a surface on one end of the substrate 11 in a thickness direction and the second surface 11T constitutes a surface on the other end of the substrate 11 in the thickness direction.

Preferably, the piercing projection 12 has a thinness and a tip angle sufficient to puncture the skin of a target for drug administration and a length sufficient to deliver a drug into the skin. Accordingly, the piercing projection 12 preferably has a cross sectional area which decreases toward the tip. For example, the piercing projection 12 has a conical or pyramidal shape. Further, the piercing projection 12 may be shaped as a combination of two or more three dimensional shapes, for example, a cone stacked on a cylinder. Moreover, the piercing projection 12 may have a narrow portion or roughness on a side wall.

The piercing projection 12 has a length Hn in the thickness direction of the substrate 11, that is, a length from the first surface 11S to the tip of the piercing projection 12 in a direction perpendicular to the first surface 11S of the substrate 11. The length Hn of the piercing projection 12 is preferably in such a range that penetrates the stratum corneum, which is the outermost layer of the skin, and does not reach nerves. Specifically, the length Hn is preferably in a range of 0.05 mm or more and 3 mm or less. Further, the piercing projection 12 has a width D in a direction along the first surface 11S, which is preferably in a range of 0.005 mm or more and 2 mm or less. The width D is a maximum length of a junction between the substrate 11 and the piercing projection 12 in a cross section taken along the thickness direction of the substrate 11, that is, a maximum length of a bottom of the piercing projection 12 located on the first surface 11S. The number of the piercing projection 12 is not limited, and may be one or more.

The non-piercing projection 13 may be in any shape. The non-piercing projection 13 may have a cylinder or prism shape or a cone or pyramid shape. However, the tip of the non-piercing projection 13 is preferably flatter than the tip of the piercing projection 12, and more preferably, the tip surface of the non-piercing projection 13 is a flat surface. From this point of view, the non-piercing projection 13 is preferably in a cylinder or prism shape.

The non-piercing projection 13 has a length Ht, which is a length from the first surface 11S to the tip of the non-piercing projection 13 in the thickness direction of the substrate 11. The length Ht of the non-piercing projection 13 is smaller than the length Hn of the piercing projection 12. In order to ensure a large length of a portion of the piercing projection 12 which is available for drug administration, the length Ht of the non-piercing projection 13 is preferably one-fourth or less of the length Hn of the piercing projection 12.

Although a lower limit of the length Ht of the non-piercing projection 13 is not specifically limited, the length Ht of the non-piercing projection 13 is preferably larger than the height of a bump of the waviness or roughness of the first surface 11S which is generated during manufacturing process of the microneedle 10. From this point of view, the length Ht of the non-piercing projection 13 is preferably 50 µm or more.

The width of the non-piercing projection 13 in a direction along the first surface 11S is not specifically limited.

As shown in FIG. 2, when the microneedle 10 includes a plurality of piercing projections 12, each of the plurality of piercing projections 12 may be arranged regularly or irregularly on the first surface 11S of the substrate 11. For example, the plurality of piercing projections 12 is arrayed in a matrix or concentric pattern as seen in a direction perpendicular to the first surface 11S. In FIG. 2, the piercing projections 12 are arrayed in a matrix pattern in an octagonal area.

The non-piercing projections 13 are disposed on an outer periphery which surrounds the piercing projections 12 on the first surface 11S of the substrate 11. That is, the non-piercing projections 13 are disposed outside of the area in which the piercing projections 12 are disposed. In this embodiment, the microneedle 10 includes three non-piercing projections 13 such that the piercing projections 12 protrude from a plane that includes the tips of the three non-piercing projections 13. That is, the piercing projections 12 protrude beyond the plane that includes the tips of the three non-piercing projections 13. The three non-piercing projections 13 constitute a group of non-piercing projections, which is an example of a group of surface-defining structures.

As seen in the direction perpendicular to the first surface 11S, an area surrounded by straight lines that connect the three non-piercing projections 13 is a target area. It is preferable that a shape formed by connecting the outermost piercing projections 12 in the area where the piercing projections 12 are disposed has a center of gravity in the target area as seen in the direction perpendicular to the first surface 11S. In other words, when a shape having the center of gravity in the target area is a target shape, the piercing projection 12 is preferably disposed at a vertex of the target shape. For example, in FIG. 2, a center of gravity A of an octagon formed by connecting the outermost piercing projections 12 is disposed in the triangular area formed by straight lines that connect three non-piercing projections 13.

In particular, when the substrate 11 is a disc shape, the plurality of non-piercing projections 13 are preferably disposed on the outer periphery of the first surface 11S equally spaced in the circumferential direction of the substrate 11.

The administration method using the microneedle 10 is not specifically limited. For example, a liquid drug may be applied on the skin before of after the microneedle 10 is pierced into the skin so that the drug is delivered into the skin through the holes formed by the piercing projections 12. Alternatively, a drug may be applied on the surface of the piercing projections 12 so that the drug is delivered into the skin when the piercing projections 12 pierce the skin, or a drug may be contained in the piercing projections 12 so that the drug is delivered into the skin when the piercing projections 12 are dissolved while being pierced into the skin. Further alternatively, a liquid drug may be externally supplied to the microneedle 10 so that the the drug is delivered into the skin through the piercing projections 12. In this case, the microneedle 10 has a through hole that penetrates from the tip of the piercing projection 12 to the second surface 11T of the substrate 11 so that the drug is delivered into the skin through the through hole.

The type of the drug is not specifically limited as long as it works when administered into the skin, and may be, for example, pharmacologically active agents such as vaccines or cosmetic compositions having aesthetic effect. The administration target of the drug is not specifically limited, and may be any animal including a human.

Manufacturing Method for Microneedle

With reference to FIGS. 3 to 6, a method for manufacturing the microneedle 10 will be described.

Figure 3:
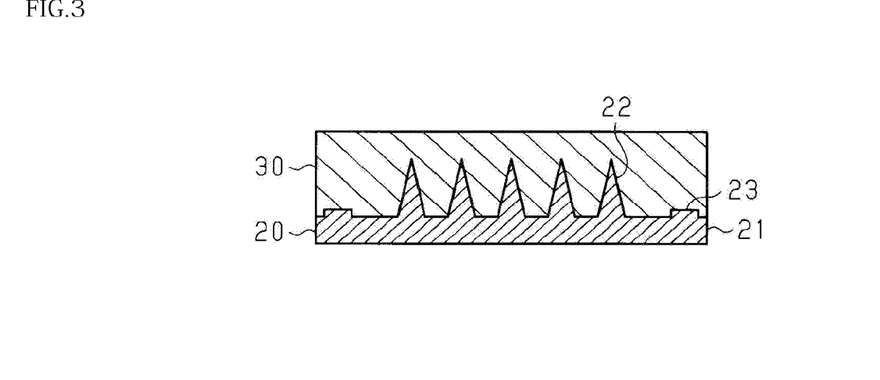
FIG. 3 is a view which shows a manufacturing step of a microneedle of an embodiment, showing that an intaglio plate is produced from an original plate.

As shown in FIG. 3, an original plate 20 for the microneedle 10 is first produced. The original plate 20 includes a substrate 21 having the same outer shape as that of the resultant substrate 11 of the microneedle 10, first original plate projections 22 having the same shape and the same arrangement as those of the piercing projections 12 of the microneedle 10, and second original plate projections 23 having the same shape and the same arrangement as those of the non-piercing projections 13 of the microneedle 10. From this original plate 20, the microneedles 10 having the identical shape are manufactured in a large quantity.

In addition, the original plate 20 may also be used as a microneedle of a resultant product as well as the microneedles 10 manufactured by using the original plate 20.

The original plate 20 is formed by cutting or adding a forming material of the original plate 20. For example, the forming material may be ground by operating an inclined blade for a plurality of times to form the first original plate projections 22 or the second original plate projections 23, or alternatively, the original plate 20 may be fabricated by micromachining using a 5-axis machining system or the like. Alternatively, the forming material may be etched by dry etching, wet etching or the like to fabricate the original plate 20.

The forming material of the original plate 20 is not specifically limited, and materials such as a metal, ceramics, silicon, glass and the like may be advantageously used. When the original plate 20 is used as a microneedle of a resultant product, the original plate 20 is preferably made of a material having a strength and biocompatibility required for puncturing of the skin.

Further, the second original plate projections 23 may also be fabricated separately from the substrate 21 and the first original plate projections 22, and the second original plate projections 23 may be fixed to the substrate 21 by welding, adhesion or the like.

Figure 4:
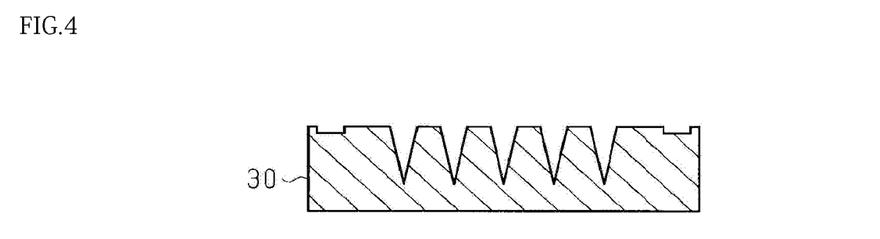
FIG. 4 is a view which shows a manufacturing step of a microneedle of an embodiment, showing the produced intaglio plate.

Subsequently, mold making of the original plate 20 is performed to produce an intaglio plate 30.

As shown in FIG. 4, the intaglio plate 30 has a reversed pattern of raised and recessed portions of the original plate 20. The forming material of the intaglio plate 30 is not specifically limited. For example, a metal such as Ni or a resin such as silicone rubber may be advantageously used.

Figure 5:
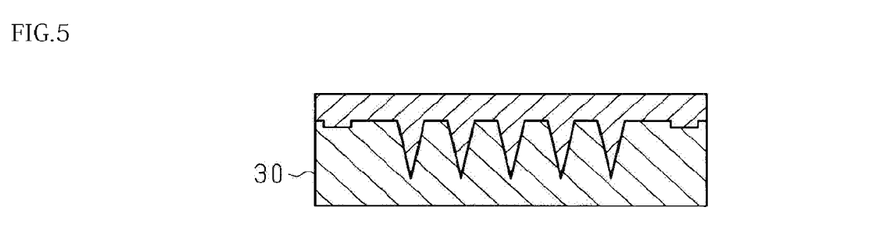
FIG. 5 is a view which shows a manufacturing step of a microneedle of an embodiment, showing that the intaglio plate is filled with a forming material of a microneedle.

As shown in FIG. 5, the intaglio plate 30 is then filled with the forming material of the microneedle 10.

The forming material of the microneedle 10 is preferably a biocompatible material. In particular, since the surface of the substrate 11 is likely to be waved when the microneedle 10 is made of a resin, the configuration of the present embodiment can be effectively applied to such a microneedle 10. Examples of the biocompatible resin material include medical grade silicone, polylactic acid, polyglycol acid, polycarbonate, PEEK material and the like.

The intaglio plate 30 is, for example, filled with the melted forming material. When the forming material is a thermoplastic resin, molding can be performed in a short period of time by appropriately managing temperature increase and decrease. In so doing, a pressure can be applied to the resin so that the resin is forced into the intaglio plate 30. This allows for molding in shorter period of time.

Figure 6:
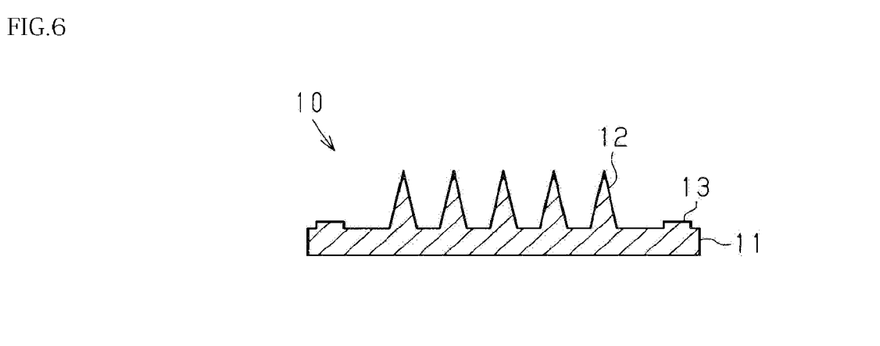
FIG. 6 is a view which shows a manufacturing step of a microneedle of an embodiment, showing a microneedle, which is a molded product, removed from the intaglio plate.

As shown in FIG. 6, the molded product is removed from the intaglio plate 30 to obtain the microneedle 10. Removal of the molded product is performed by suctioning the surface of the molded product exposed from the intaglio plate 30 by using a vacuum machine, or by adhering an adhesive subject on the surface of the molded product exposed from the intaglio plate 30 and peeling off the molded product from the intaglio plate 30. Alternatively, the molded product may be pushed out from the intaglio plate 30 by using an ejecter pin.

Furthermore, the forming material and the manufacturing method for the microneedle 10 are not limited to the above example as long as the microneedle 10 having the configuration described above with reference to FIGS. 1 and 2 can be produced. For example, the forming material may be a metal such as stainless steel, titanium, manganese or silicon, or ceramic such as alumina, zirconia, silicon carbide or silicon nitride. When the piercing projection 12 contains a drug and is dissolved in the skin, the forming material may be a water soluble polymer. The microneedle 10 may be produced by a manufacturing method appropriate for the forming materials. Structure of microneedle assembly With reference to FIGS. 7 and 8, a structure of the microneedle assembly as well as an effect brought by the microneedle and the microneedle assembly of the present embodiment will be described.

Figure 7:
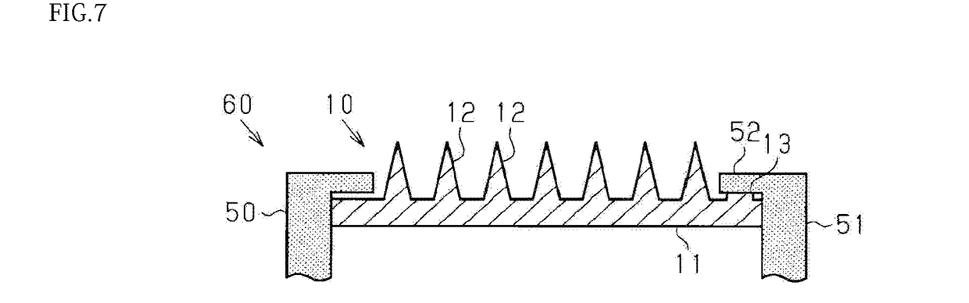
FIG. 7 is a cross sectional view which shows a partial cross sectional structure of a microneedle assembly according to an embodiment.

As shown in FIG. 7, a microneedle assembly 60 includes the above microneedle 10 and an applicator 50. The applicator 50 includes a cylinder portion 51 having two opening ends and an inner cylindrical space between the opening ends, and the cylinder portion 51 includes a support portion 52 that forms one of the two opening ends of the cylinder portion 51 and inwardly projects in a radial direction of the cylinder portion 51.

When the microneedle 10 and the applicator 50 are assembled together, the substrate 11 is housed in the inner cylindrical space of the cylinder portion 51 with the first surface 11S of the substrate 11 oriented to the support portion 52. The piercing projections 12 protrude outside the applicator 50 from the opening end, which is the support portion 52.

The applicator 50 has a function of assisting puncturing of the skin by the piercing projections 12. For example, the applicator 50 may include a portion that serves as a grip for a user when the user pierces the microneedle 10 into the skin, or a mechanism that imparts a biasing force to the piercing projection 12 for puncturing the skin.

Figure 8:
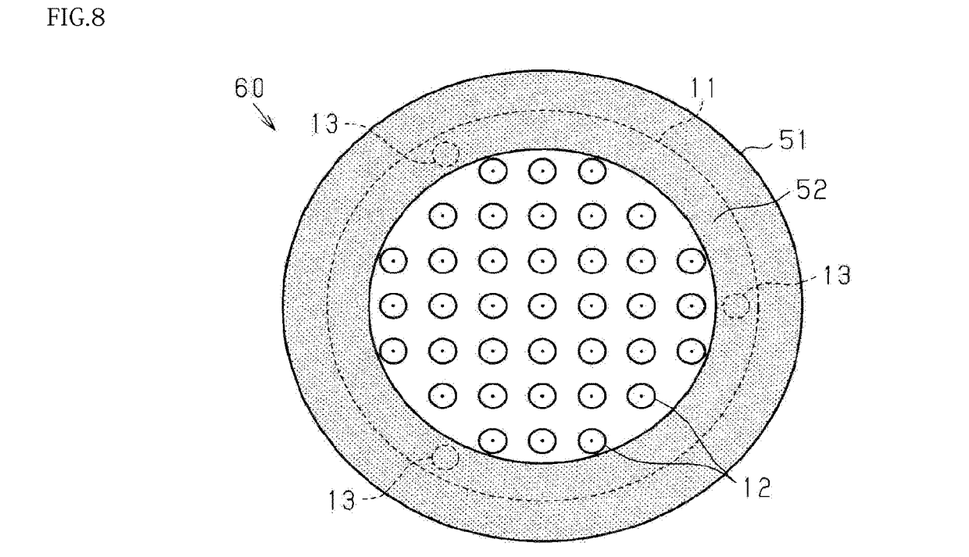
FIG. 8 is a plan view which shows a planar structure of a microneedle assembly according to an embodiment.

As shown in FIG. 8, as seen in the direction perpendicular to the first surface 11S of the substrate 11, an outline of an area surrounded by an inner peripheral edge of the support portion 52 is smaller than an outline of the substrate 11 and larger than an outline of an area on which the piercing projections 12 are formed on the first surface 11S. For example, when the outline of the substrate 11 is a circular shape, the outline of the area surrounded by the inner peripheral edge of the support portion 52 is concentric with and smaller than the circle of the outline of the substrate 11. Moreover, the outer periphery of the substrate 11 on which the non-piercing projections 13 are formed is covered by the support portion 52.

In this configuration, the piercing projections 12 protrude outside the cylinder portion 51 from the area surrounded by the inner peripheral edge of the support portion 52, and the tips of the non-piercing projections 13 are in contact with the support portion 52 in the inner cylindrical space of the cylinder portion 51. That is, the support portion 52 is always located on a plane including the tips of three non-piercing projections 13.

As described above, when the three non-piercing projections 13 are formed on the first surface 11S of the substrate 11, a single plane which includes the tips of the three non-piercing projections 13 is defined and the plane serves as a reference surface. Further, the length from the reference surface to the tip of the piercing projection 12 is determined as a single value for the respective piercing projections 12. When the microneedle 10 and the applicator 50 are assembled together, the applicator 50 is in position with respect to the reference surface. Accordingly, even if the substrate 11 has a waviness or curvature, the length of the piercing projections 12 which protrude outside the applicator 50 is constant for the respective piercing projections 12 and does not vary every time when the microneedle 10 and the applicator 50 are assembled together.

As a result, improvement in stability of the length and the number of the piercing projections 12 pierced into the skin and the sizes of the holes formed by puncture contributes for improvement in stability in piercing functions of the piercing projections 12 in drug administration.

Moreover, it is also possible to obtain the length of the piercing projection 12 which protrudes outside from the applicator 50 from elements defined by the applicator, such as a reference length, which is a length from the reference surface to the tip of the piercing projection 12, or the thickness of the support portion 52 by calculating the reference length in advance on the basis of the length Hn of the piercing projection 12 or the length Ht of the non-piercing projection 13.

In addition, when a pretreatment or a post treatment is performed before or after the microneedle 10 is pierced into the administration target, the microneedle 10 is preferably installed in position according to the reference surface in a device that performs a pretreatment or a post treatment. According to this configuration, the length of the piercing projection 12 having a pretreatment or a post treatment can be prevented from varying every time when the microneedle 10 is installed in the device.

As described above, according to the microneedle and the microneedle assembly of the present embodiment, the following effect can be achieved.

(1) Since three non-piercing projections 13 are disposed on the outer periphery on the first surface 11S of the substrate 11, a single plane which includes the tips of the three non-piercing projections 13 is defined and the plane serves as a reference surface. The length of the piercing projection 12 which protrudes from the reference surface is determined with respect to the reference surface. Accordingly, the applicator 50 can be positioned with respect to the reference surface, thereby improving the stability in piercing functions of the piercing projections 12 in drug administration. In particular, since three non-piercing projections 13 are provided, a single plane is accurately defined as the reference surface.

If the microneedle does not include the non-piercing projections 13, the length of the piercing projections 12 exposed from the applicator 50 may vary depending on with which portion of the first surface 11S of the substrate 11 the support portion 52 of the applicator 50 is in contact when the first surface 11S of the substrate 11 has a slight waviness or a small curvature and is not completely flat. Accordingly, even if an inspection is conducted to inspect the length of the piercing projections 12 exposed from the applicator 50 and the variation in lengths before the microneedle is loaded in the applicator 50 in attempt to screen out the microneedles having the length of the piercing projection 12 and the variation in lengths which do not meet the reference value, this screening is difficult since the length of the piercing projection 12 and the variation in lengths vary every time when the microneedle is loaded in the applicator 50. According to the microneedle 10 of the present embodiment, a single plane is accurately defined as the reference surface, and thus the length of a portion of the piercing projection 12 which protrudes from the reference surface is determined as a single value. As a result, by positioning the applicator 50 with respect to the reference surface and by using the length of a portion protruding from the reference surface for an inspection, the microneedles having the length of the piercing projection 12 exposed from the applicator 50 and the variation in lengths which do not meet the reference value can be easily screened out before the microneedle is loaded in the applicator 50.

Further, since the substrate 11, the piercing projections 12 and the non-piercing projections 13 are formed in unity, the microneedle 10 having the non-piercing projections 13 can be easily manufactured.

(2) Since the tip of the non-piercing projection 13 is flatter than the tip of the piercing projection 12, measurement of the tip of the non-piercing projection 13 is easier than measurement of the tip of the piercing projection 12. Accordingly, a plane which includes the tips of three non-piercing projections 13 can be easily defined.

(3) Since the tip surface of the non-piercing projection 13 is a flat surface, a position of the non-piercing projection 13 is easily measured. Further, since the non-piercing projection 13 is in surface contact with the support portion 52 of the applicator 50, positional stability between the microneedle 10 and the applicator 50 is improved when the microneedle 10 and the applicator 50 are assembled together.

(4) When a shape having the center of gravity in an area surrounded by straight lines that connect the adjacent non-piercing projections 13 as seen in the direction perpendicular to the first surface 11S of the substrate 11, the piercing projection 12 is disposed at a vertex of the target shape. With this configuration, the non-piercing projections 13 are prevented from being unevenly positioned on the outer periphery of the substrate 11 with respect to the arrangement of the piercing projection 12. Accordingly, the piercing projections 12 are prevented from being unevenly positioned with respect to the plane defined by the non-piercing projections 13. Further, when the microneedle 10 is used assembled to the applicator 50, the non-piercing projections 13 are in contact with the applicator 50 with a good balance to the positions of the piercing projections 12 on the outside of the area in which the piercing projections 12 are disposed. Accordingly, positional stability of the piercing projections 12 which protrude outside the applicator 50 is improved. In particular, in a configuration in which the substrate 11 is a disc shape and a plurality of non-piercing projections 13 are disposed on the outer periphery of the first surface 11S equally spaced in the circumferential direction of the substrate 11, positional stability of the piercing projections 12 is further improved.

Modified Example

The above embodiment can be implemented with modifications as described below.

Figure 9:
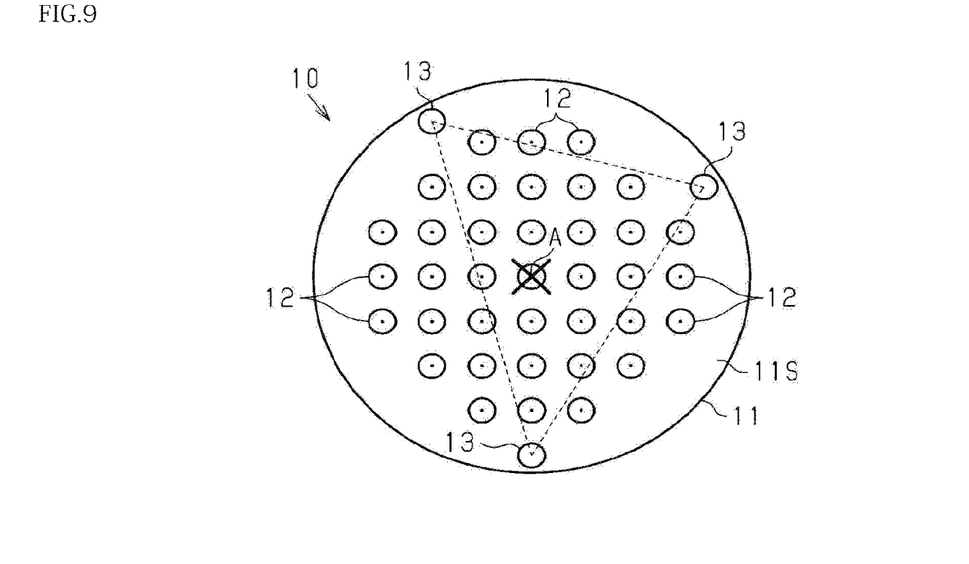
FIG. 9 is a plan view which shows a planar structure of a microneedle according to a modified example.

As shown in FIG. 9, the plurality of non-piercing projections 13 may not necessarily be evenly distributed in the circumferential direction of the substrate 11 on the outer peripheral region of the first surface 11S. In this configuration, the plurality of non-piercing projections 13 can be used as alignment marks for positioning the microneedle 10 in manufacturing or use of the microneedle 10. In the case where the plurality of non-piercing projections 13 is not evenly distributed, it is also preferable that the piercing projection 12 is disposed at a vertex of the target shape while the target shape has a center of gravity in a target area surrounded by straight lines that connect the adjacent non-piercing projections 13 on the outer peripheral region of the substrate 11 as seen in the direction perpendicular to the first surface 11S. Furthermore, the effect of the above (1) can be achieved even if the piercing projection 12 is not disposed at a vertex of the target shape having the center of gravity described above.

Figure 10:
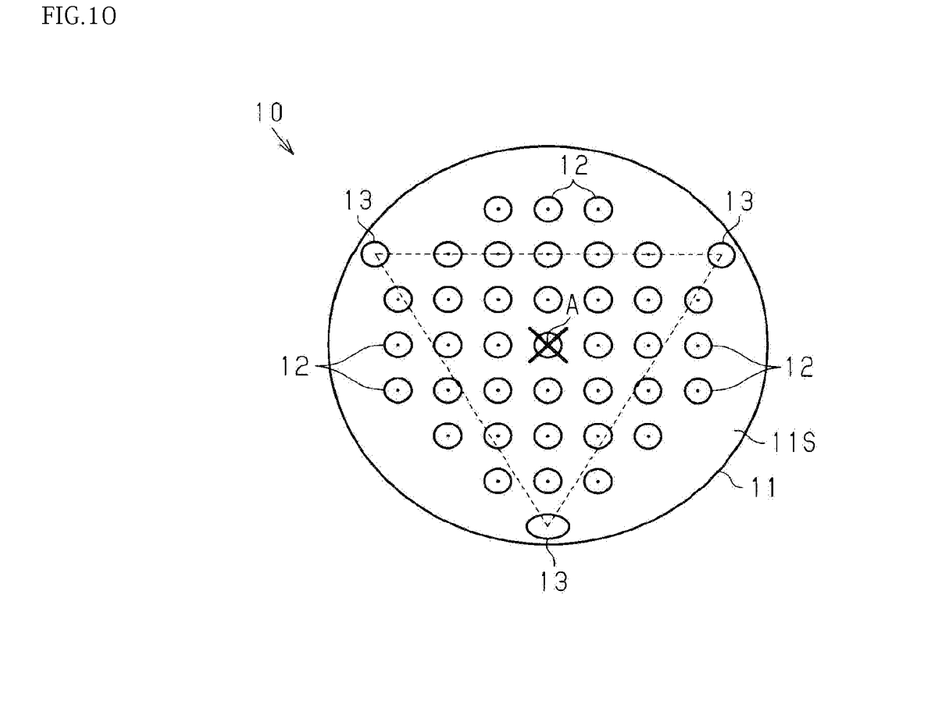
FIG. 10 is a plan view which shows a planar structure of a microneedle according to a modified example.

As shown in FIG. 10, the plurality of non-piercing projections 13 may include the non-piercing projection 13 having a shape different from that of the other non-piercing projections 13, or alternatively, the plurality of non-piercing projections 13 may be different in shape from each other. For example, FIG. 10 shows an example which includes three non-piercing projections 13, one of which is formed in a cylindrical shape having an oblong cross section and two of which are formed in a cylindrical shape having a circular cross section. In this configuration, the non-piercing projections 13 can be used as alignment marks for positioning the microneedle 10 in manufacturing or use of the microneedle 10.

Figure 11:
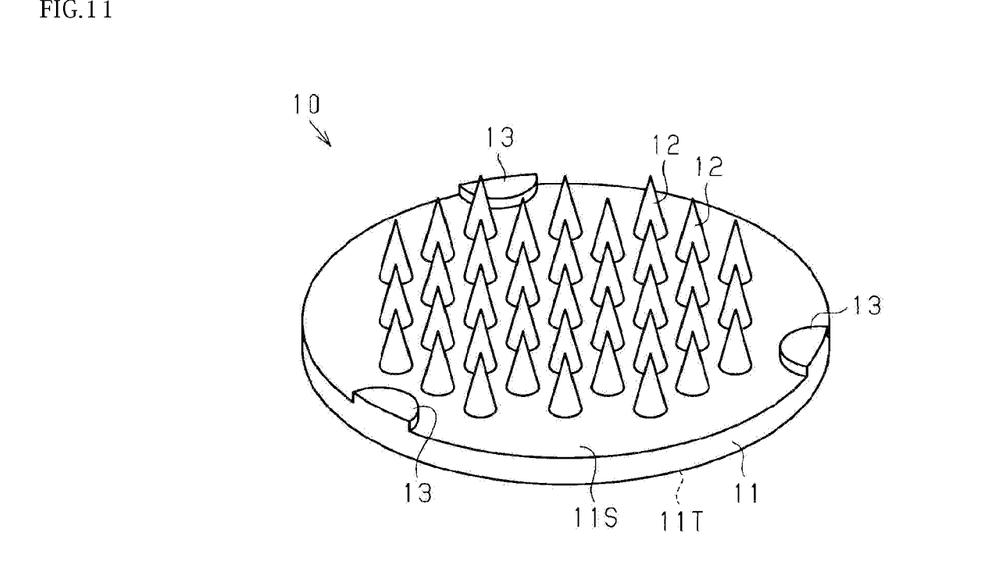
FIG. 11 is a perspective view which shows a perspective structure of a microneedle according to a modified example.

Further, as shown in FIG. 11, the non-piercing projections 13 may also be in contact with the outer edge of the first surface 11S of the substrate 11. That is, as seen in the direction perpendicular to the first surface 11S, the outer edge of the non-piercing projection 13 and the outer edge of the substrate 11 may be partially overlapped. When the microneedle 10 and the applicator 50 are assembled together, the support portion 52 of the applicator 50 is required to be positioned so as to be in contact with the tip of the non-piercing projections 13 and not to be in contact with the first surface 11S of the substrate 11. According to the above configuration, the applicator 50 having such a positional relationship can be easily achieved. In addition, the microneedle 10 and the applicator 50 can be easily assembled.

The plurality of non-piercing projections 13 may include the non-piercing projection 13 having the length Ht different from that of the other non-piercing projections 13, or alternatively, the plurality of non-piercing projections 13 may have the length Ht different from each other. For example, when the plurality of piercing projections 12 has a length Hn which decreases toward a predetermined location, the plurality of non-piercing projection 13 may have a length Ht which decreases toward the predetermined location. In this configuration, distribution of the lengths of the piercing projections 12 which is available for drug administration can be adjusted.

The tip surface of the non-piercing projection 13 may be a curved surface as long as it is flatter than the tip of the piercing projection 12. For example, the non-piercing projection 13 may have a cone shape. In this case, the tip of the non-piercing projection 13 preferably has a radius of curvature larger than the tip of the piercing projection 12. In this configuration as well, a single reference surface is defined by the tips of three non-piercing projections 13. Furthermore, a single reference surface is defined by the tips of three non-piercing projections 13 even if the tip of the non-piercing projection 13 is not flatter than the tip of the piercing projection 12.

Figure 12:
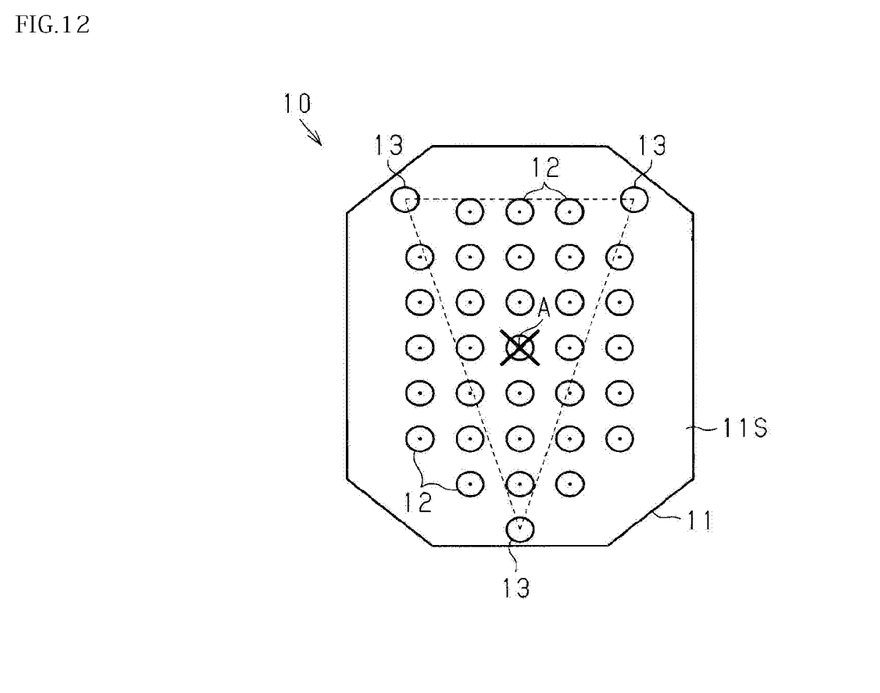
FIG. 12 is a plan view which shows a planar structure of a microneedle according to a modified example.

As shown in FIG. 12, the outline of the substrate 11 is not limited to a circular shape, but may be a polygonal shape. In this case, the cylinder portion 51 of the applicator 50 is in a cylindrical shape with a cross section having an inner peripheral edge of a similar shape to the outline of the substrate 11. The support portion 52 covers the outer peripheral region of the substrate 11, that is, a region outside the portion on which the piercing projections 12 are formed and is in contact with the non-piercing projections 13.

The number of the non-piercing projections 13 that constitute the group of non-piercing projections is four or more, and preferably, three or more and five or less. It is preferable that the three or more and five or less non-piercing projections 13 are distributed across the entire outer peripheral region of the first surface 11S. However, as shown in the above embodiment, the number of the non-piercing projections 13 distributed across the entire outer peripheral region of the first surface 11S is most preferably three.

When the number of non-piercing projections 13 is four or more, a plurality of planes which contains any three of the non-piercing projection 13 may be defined so that the piercing projections 12 protrude from each of the plurality of planes. When the number of non-piercing projections 13 that constitute the group of non-piercing projections is three or more and five or less, the number of planes which includes the tips of any three of the non-piercing projections 13 is smaller than that when the number of non-piercing projections 13 is five or more. Accordingly, such planes can be defined easily. Further, when the non-piercing projections 13 that constitute the group of non-piercing projections are distributed across the entire outer peripheral region of the first surface 11S, the general shape of the outer peripheral region can be reflected on the defined surface compared with the configuration in which the non-piercing projections 13 are unevenly positioned on the outer peripheral region.

When the plurality of planes is defined, it is preferable that a single plane is selected as a reference surface out of these planes. For example, a surface by which the length of the piercing projection 12 which is available for drug administration is closest to a desired length is selected as a reference surface, and accordingly, three non-piercing projections 13 that constitute the selected plane are selected as the non-piercing projections 13 that constitute the reference surface.

For example, the support portion 52 of the applicator 50 may be disposed at a position that is in contact with three non-piercing projections 13 located at predetermined positions in the outer peripheral region of the substrate 11 and is not in contact with the non-piercing projections 13 located at the other positions. In this configuration as well, a single plane is selected as a reference surface out of the plurality of planes defined by the plurality of non-piercing projections 13. In this case, the position of the support portion 52 can be configured to be changed or the three non-piercing projections 13 that constitute the reference surface can be configured to be changed, for example, according to the type of the applicator 50.

Further, three non-piercing projections 13 and a large number of non-piercing projections 13 having the length smaller than the length Ht of the three non-piercing projections 13 may be disposed on the first surface 11S of the outer peripheral region of the substrate 11. In this configuration, when the microneedle 10 and the applicator 50 are pressed against the skin, the substrate 11 is pressed against the support portion 52 and thus the non-piercing projections 13 other than the three non-piercing projections 13 having the length Ht which is relatively longer among the plurality of non-piercing projections 13 are also in contact with the support portion 52. As a result, compared with the case where only three non-piercing projections 13 are provided, an area of a portion of the microneedle 10 which receives a load from the support portion 52 increases, thereby preventing deformation such as warpage of the substrate 11 from occurring in the microneedle 10.

Further, in addition to the non-piercing projections 13 disposed in the outer peripheral region of the substrate 11, the non-piercing projection 13 may also be provided at a position other than the outer peripheral region of the substrate 11.

In the above embodiment, the substrate 11, the piercing projections 12 and the non-piercing projections 13 are formed in unity. However, the non-piercing projections 13 may be formed separately from the substrate 11 and the piercing projections 12 and then fixed to the first surface 11S of the substrate 11. The non-piercing projections 13 are made of a material similar to that of the substrate 11 and the piercing projections 12, such as biocompatible metal or resin, and fixed to the first surface 11S by adhesion or the like. In this configuration, since the shape or arrangement of the non-piercing projections 13 can be easily changed for each microneedle 10, the shape or arrangement of the non-piercing projections 13 can be easily adjusted.

The above embodiment and modified examples describe an example in which the surface-defining structures are projections which protrude from the first surface 11S of the substrate 11, that is, the non-piercing projections 13, and the tips of the non-piercing projections 13 serve as the surface-defining sections that define a plane. The surface-defining structures that constitute the group of surface-defining structures are not limited to the above example, and may have any configuration in that the surface-defining structures are different in height with respect to the first surface 11S and a single plane can be defined by points included in the surfaces of the respective three surface-defining structures.

Figure 13:
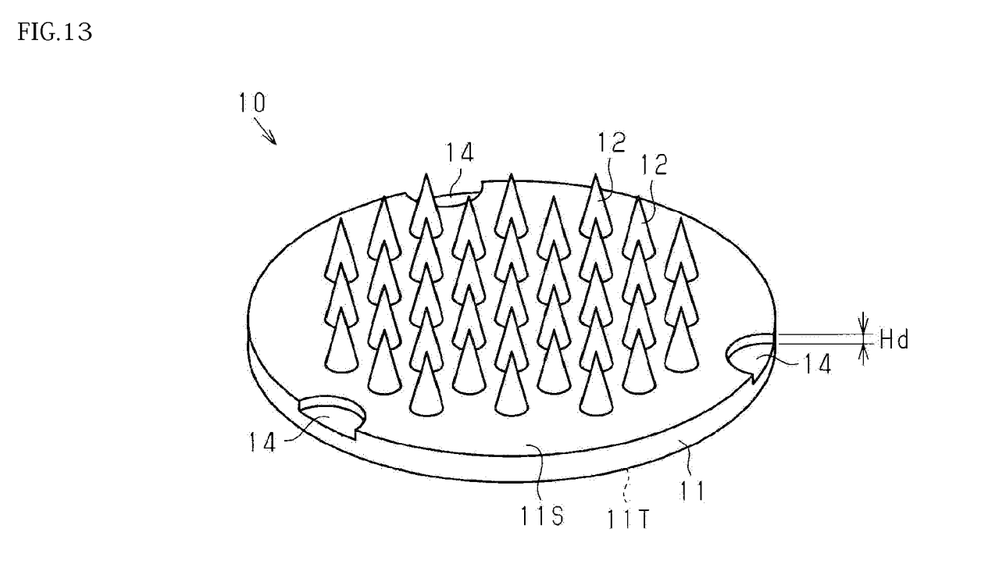
FIG. 13 is a perspective view which shows a perspective structure of a microneedle according to a modified example.

That is, as shown in FIG. 13, the surface-defining structure may also be a recess 14 which is the surface-defining recess recessed from the first surface 11S. In this case, a bottom of the recess 14 serves as the surface-defining section. The support portion 52 of the applicator 50 assembled to the microneedle 10 having the above configuration has, for example, a projection that protrudes toward the first surface 11S from a surface of the support portion 52 which faces the first surface 11S. When the microneedle 10 and the applicator 50 are assembled together, the projection comes into contact with the bottom of the recess 14. That is, the support portion 52 is always disposed on a plane that includes the bottoms of three recesses 14. In this configuration as well, the length of the piercing projections 12 that protrude from the reference surface defined by the bottoms of the three recess 14 can be determined with respect to the reference surface. Accordingly, stability in piercing functions of the piercing projections 12 in drug administration can be improved.

Similar to the case where the surface-defining structure is the non-piercing projection 13, the bottom of the recess 14 is preferably flatter than the tip of the piercing projection 12, and the bottom of the recess 14 is preferably a flat surface as shown in FIG. 13. As shown in the above embodiment and modified examples, the recesses 14 are preferably positioned in a similar manner to the case where the surface-defining structure is the non-piercing projection 13. Specifically, the following positioning is preferable.

That is, as shown in FIG. 13, the recesses 14 are disposed at positions on the outer edge of the substrate 11, and the outer edge of the recess 14 and the outer edge of the substrate 11 are partially overlapped as seen in the direction perpendicular to the first surface 11S. When the microneedle 10 and the applicator 50 are assembled together, the support portion 52 of the applicator 50 is required to be positioned so as to be in contact with the bottoms of the recesses 14 and not to be in contact with the first surface 11S of the substrate 11. According to the above configuration, the applicator 50 having such a positional relationship can be easily achieved. In addition, the microneedle 10 and the applicator 50 can be easily assembled.

A depth Hd of the recess 14, which is a length from the first surface 11S to the bottom of the recess 14, in the thickness direction of the substrate 11 is preferably larger than the depth of a dent of the waviness or roughness of the first surface 11S which is generated during manufacturing process of the microneedle 10. From this point of view, the depth Hd of the recess 14 is preferably 50 µm or more.

Further, similar to the case where the surface-defining structure is the non-piercing projection 13, the number of recesses 14 that constitute the group of surface-defining structures is preferably three or more and five or less. It is preferable that the three or more and five or less recesses 14 are distributed across the entire outer peripheral region of the substrate 11. Further, the number of the recesses 14 distributed across the entire outer peripheral region of the substrate 11 is preferably three.

Further, similar to the case where the surface-defining structure is the non-piercing projection 13, it is preferable that the piercing projection 12 is disposed at a vertex of the target shape when the target shape is a shape having the center of gravity in the target area surrounded by straight lines that connect the adjacent recesses 14 in the outer peripheral region as seen in the direction perpendicular to the first surface 11S.

Further, in comparison of the configuration in which the surface-defining structure is the non-piercing projection 13 that protrudes from the first surface 11S of the substrate 11 and the configuration in which the surface-defining structure is the recess 14 that is recessed from the first surface 11S, the configuration in which the surface-defining structure is the non-piercing projection 13 is more preferable since the length of the piercing projection 12 protruding from the reference surface can be measured easier and the surface-defining section can be formed flat easier. However, a portion of the piercing projection 12 which protrudes from the reference surface can be larger and the length of the portion which is available for drug administration can be larger in the configuration in which the surface-defining structure is the recess 14.

EXAMPLE

The above microneedle and the microneedle assembly will be described by using a specific example.

Manufacturing of Microneedle

First, the original plate 20 for the microneedle 10 was produced. Quartz was used as a forming material for the original plate 20, and the original plate 20 was formed by using a 5-axis machining center.

The first original plate projections 22 disposed on the original plate 20 were 37 in total, composed of the projections arranged in a 5×5 matrix and three projections disposed on each of the upper, lower, right and left outside of the square formed by the 5×5 matrix. That is, as shown in FIG. 2, the first original plate projections 22 were arranged in a matrix array in an octagonal area. The first original plate projection 22 was formed in a cone shape, and had a length of 900 µm and a width of 400 µm. A pitch between the adjacent first original plate projections 22 was 700 µm. An outline of the substrate 21 was a circle with a diameter of 6.2 mm, and a thickness of the substrate 21 was 1000 µm.

The second original plate projection 23 on the original plate 20 had a cylindrical shape, and the tip of the second original plate projection 23 had a flat surface. The second original plate projection 23 had a length of 100 μm and a width of 400 μm. The number of the second original plate projections 23 was three. As shown in FIG. 2, the three second original plate projections 23 were evenly positioned in the outer peripheral region of the substrate 21 in the circumferential direction of the substrate 21. The three second original plate projections 23 had the identical shape.

Then, the intaglio plate 30 was produced from the original plate 20. Specifically, a Ni layer was formed on the surface of the original plate 20 by Ni electrocasting, and then the original plate 20 was removed by hydrofluoric acid to form an Ni intaglio plate 30.

Then, a PGA, which is one of medical grade biodegradable resins, was placed as a forming material for the microneedle 10 on the intaglio plate 30, and heated at 250° C. to melt the PGA. The amount of the PGA was adjusted depending on the shape of the microneedle 10 for the application purpose and the thickness of the substrate 11. Subsequently, the PGA was pressurized from the above by using a silicone rubber roller to be pushed into the intaglio plate 30.

Then, the intaglio plate 30 in which the PGA was filled was cooled from the above and below. After the temperature of the intaglio plate 30 was lowered close to room temperature, vacuum tweezers were mounted on the backside of the molded product to peel off the molded product from the intaglio plate 30. In order to prevent the tip of the piercing projection 12 from being bent or curved, it is preferable to peel off the molded product perpendicularly to the intaglio plate 30.

As a result, the piercing projections 12 were disposed at positions corresponding to the first original plate projections 22 of the original plate 20. The microneedle provided with the piercing projection 12 having the length Hn of 900 μm and the width D of 400 μm and the substrate 11 having the thickness of 400 μm was obtained. The three cylindrical non-piercing projections 13 were disposed in the outer peripheral region of the first surface 11S of the substrate 11 at positions corresponding to the second original plate projections 23 of the original plate 20. The three non-piercing projections 13 were evenly positioned in the circumferential direction of the substrate 11 and the length Ht of the non-piercing projection 13 was 100 μm.

Manufacturing of microneedle assembly

A microneedle assembly 60 of the Example was obtained by assembling the microneedle 10 of the Example to the applicator 50. As shown in FIG. 7, the applicator 50 included the cylinder portion 51 having a cylindrical shape and the support portion 52. An inner diameter of the cylinder portion 51 was 6.2 mm, and an inner diameter of the support portion 52 was 5 mm, and a thickness of the support portion 52 was 300 μm.

As a result of assembling the microneedle 10 to the applicator 50, the non-piercing projections 13 were in contact with the support portions 52 at positions inside the cylinder portion 51, and the support portion 52 was disposed on a single plane which includes the tips of the three non-piercing projections 13.

Accordingly, the distribution of the lengths of the piercing projections 12 which protrude from the applicator 50 was calculated depending on the distribution of the length Hn of the piercing projections 12 and the lengths Ht of the non-piercing projections 13 measured in advance. In this Example, the length of the piercing projections 12 which protrude from the applicator 50 was 500 μm.

According to a drug administration method using a microneedle, a microneedle assembly which includes a microneedle and an applicator that guides the piercing projections to puncture the skin is used. The applicator supports an outer periphery of one of two surfaces of the substrate, the surface on which the piercing projections are formed, so that the piercing projections exposed from the applicator are subject to a biasing force via the applicator to puncture the skin.

In some cases, the above substrate may have a surface which is not completely flat, for example, has a slight waviness or a small curvature. Accordingly, the length of the piercing projections exposed from the applicator varies depending on which portion of the surface of the substrate the applicator supports. This may cause a problem that the length of the piercing projections exposed from the applicator can not be determined as a single value with respect to a measurement of length, which is measured in advance, from the surface of the substrate to the tip of the piercing projection. Accordingly, there is a further need for stabilizing the length and the number of piercing projections pierced into the skin and the sizes of the holes formed by puncture, that is, improvement in stability in piercing functions of the piercing projections. Further, improvement in stability in piercing functions of the piercing projections is required not only for microneedles used with applicators, but also for microneedles having a piercing projection on the substrate.

One aspect of the present invention is to provide a microneedle and a microneedle assembly having a piercing projection with improved stability in piercing functions in drug administration.

A microneedle for solving the above problem includes: a substrate having a first surface and a second surface which is a surface opposite from the first surface; a piercing projection projecting from the first surface of the substrate; and a group of surface-defining structures including three or more surface-defining structures, each of which has a surface-defining section, the surface-defining structure being either of a surface-defining projection which protrudes from the first surface and has a tip which serves as the surface-defining section and a surface-defining recess which is recessed from the first surface and has a bottom which serves as the surface-defining section, and the surface-defining structure being located on an outer peripheral region of the substrate which is a portion surrounding the piercing projection as seen in a direction perpendicular to the first surface, wherein a tip of the piercing projection extends beyond a plane which includes the surface-defining sections of any three of the surface-defining structures of the group of surface-defining structures.

With this configuration, the tips of the piercing projections protrude from a plane which includes the surface-defining sections of any three of the surface-defining structures, and the length of the piercing projection protruding from the plane is determined with respect to the plane. Accordingly, since the applicator can be positioned, for example, with respect to the plane, the stability in piercing functions of the piercing projections in drug administration can be improved.

In the above configuration, the surface-defining structure may be the surface-defining projection.

According to this configuration, the length of the piercing projection protruding from the plane which is defined by the surface-defining structure can be easily measured compared with the case where the surface-defining structure is the surface-defining recess.

In the above configuration, the surface-defining section is preferably flatter than the tip of the piercing projection.

According to this configuration, measurement of the positions of the surface-defining section is easier than measurement of the positions of the tips of the piercing projections. Accordingly, a plane which includes the surface-defining sections of any three of the surface-defining structures can be easily defined.

In the above configuration, the group of surface-defining structures preferably includes three or more and five or less surface-defining structures which are distributed across the entire outer peripheral region.

According to this configuration, a plane which includes the surface-defining sections of any three of the surface-defining structures can be easily defined compared with the configuration in which the number of the surface-defining structures is five or more. Further, the general shape of the outer peripheral region can be reflected on the defined surface compared with the configuration in which the surface-defining structures of the group of surface-defining structures are unevenly positioned on the outer peripheral region. Accordingly, stability in piercing functions of the piercing projections in drug administration can be further improved.

In the above configuration, wherein the number of the surface-defining structures distributed across the entire outer peripheral region is preferably three.

According to this configuration, a plane can be easily defined by the surface-defining structures, and a single plane can be accurately defined.

In the above configuration, a length of the surface-defining structure in a thickness direction of the substrate is preferably one-quarter or less of the length of the piercing projection in the thickness direction of the substrate.

According to this configuration, a portion of the piercing projection which protrudes from the plane defined by the surface-defining structures can be larger and the length of the portion of the piercing projection which is available for drug administration can be larger.

In the above configuration, the microneedle preferably includes a plurality of the piercing projections, wherein a shape having a center of gravity in an area surrounded by straight lines that connect the adjacent surface-defining structures on the outer peripheral region as seen in the direction perpendicular to the first surface is a target shape, and the plurality of piercing projections includes the piercing projection disposed at a vertex of the target shape.

According to this configuration, the surface-defining structures are prevented from being unevenly positioned with respect to the arrangement of the piercing projections. Accordingly, since the positions of the piercing projections are prevented from being unevenly positioned with respect to the plane defined by the surface-defining structures, the stability in piercing functions of the piercing projections in drug administration can be further improved.

In the above configuration, the surface-defining structure may be the surface-defining recess.

According to this configuration, a portion of the piercing projection which protrudes from the plane defined by the surface-defining structures can be larger and the length of the portion of the piercing projection which is available for drug administration can be larger compared with the configuration in which the surface-defining structure is a surface-defining projection.

In the above configuration, the surface-defining section is preferably a flat surface.

According to this configuration, since the surface-defining section is a flat surface, the position of the surface-defining section can be easily measured. Further, when the applicator is positioned on the plane defined by the surface-defining structures, the stability in positional relationship between the microneedle and the applicator can be improved.

In the above configuration, the group of surface-defining structures preferably includes three or more and five or less surface-defining structures which are distributed across the entire outer peripheral region.

According to this configuration, a plane which includes the surface-defining sections of any three of the surface-defining structures can be easily defined compared with the configuration in which the number of the surface-defining structures is five or more. Further, the general shape of the outer peripheral region can be reflected on the defined surface compared with the configuration in which the surface-defining structures of the group of surface-defining structures are unevenly positioned on the outer peripheral region. Accordingly, stability in piercing functions of the piercing projections in drug administration can be further improved.

In the above configuration, the number of the surface-defining structures distributed across the entire outer peripheral region is preferably three.

According to this configuration, a plane can be easily defined by the surface-defining structures, and a single plane can be accurately defined.

In the above configuration, the microneedle preferably includes a plurality of the piercing projections, wherein a shape having a center of gravity in an area surrounded by straight lines that connect the adjacent surface-defining structures on the outer peripheral region as seen in the direction perpendicular to the first surface is a target shape, and the plurality of piercing projections includes the piercing projection disposed at a vertex of the of the target shape.

According to this configuration, the surface-defining structures are prevented from being unevenly positioned with respect to the arrangement of the piercing projections. Accordingly, since the positions of the piercing projections are prevented from being unevenly positioned with respect to the plane defined by the surface-defining structures, the stability in piercing functions of the piercing projections in drug administration can be further improved.

The microneedle assembly for solving the above problem includes the microneedle; and an applicator having a cylinder portion, wherein the cylinder portion includes two opening ends and an inner cylindrical space between the opening ends, and the substrate of the microneedle is housed in the inner cylindrical space, one of the two opening ends is a support portion having a shape which inwardly projects in a radial direction of the cylinder portion, the three surface-defining sections included in the plane is in contact with the support portion in the inner cylindrical space, and the piercing projections protrude outside the cylinder portion from the opening end which is the support portion.

With this configuration, the tips of the piercing projections protrude from a plane which includes the surface-defining sections of any three of the surface-defining structures, and the length of the piercing projection protruding from the plane is determined with respect to the plane. Since the position of the applicator is determined with respect to the plane, the stability in piercing functions of the piercing projections in drug administration can be improved.

According to an embodiment of the present invention, piercing functions of the piercing projections of a microneedle in drug administration can be further stabilized.

REFERENCE SIGNS LIST

10 . . . microneedle, 11 . . . substrate, 11S . . . first surface, 11T . . . second surface, 12 . . . piercing projection, 13 . . . non-piercing projection, 14 . . . recess, 20 . . . original plate, 30 . . . intaglio plate, 50 . . . applicator, 51 . . . cylinder portion, 52 . . . support portion, 60 . . . microneedle assembly Obviously, numerous modifications and variations of the present invention are possible in light of the above teachings. It is therefore to be understood that within the scope of the appended claims, the invention may be practiced otherwise than as specifically described herein.

What is claimed is:

1. A microneedle, comprising:
a substrate having a first surface and a second surface opposite to the first surface;
a plurality of piercing projections projecting from the first surface of the substrate and being surrounded by an outer peripheral region of the substrate when viewed in a direction perpendicular to the first surface; and
a plurality of surface-defining structures positioned in the outer peripheral region and comprising three or more surface-defining structures such that the surface-defining structures have surface-defining sections respectively and that the surface-defining sections define a plane,
wherein the plurality of surface-defining structures is formed such that tips of the piercing projections extend beyond the plane defined by the surface-defining sections and that the surface-defining sections are tips of surface-defining projections protruding from the first surface, the plurality of surface-defining structures is positioned such that straight lines connecting adjacent surface-defining structures in the outer peripheral region form a target area when viewed in the direction perpendicular to the first surface, and the plurality of piercing projections is arrayed in a target shape such that the plurality of piercing projections includes a plurality of outermost piercing projections distributed outside the target area.

2. The microneedle of claim 1, wherein the surface-defining sections are flatter than the tips of the piercing projections.

3. The microneedle of claim 2, wherein the plurality of surface-defining structures includes three to five surface-defining structures which are distributed across an entire outer peripheral region.

4. The microneedle of claim 2, wherein the surface-defining structures each have a length equal to one-quarter or less of a length of the piercing projections in a thickness direction of the substrate.

5. A microneedle assembly, comprising:
the microneedle of claim 2, and
an applicator having a cylinder portion includes two opening ends and an inner cylindrical space between the opening ends,
wherein the substrate of the microneedle is housed in the inner cylindrical space, one of the two opening ends is a support portion having a shape which inwardly projects in a radial direction of the cylinder portion, three of the surface-defining sections defining the plane are in contact with the support portion in the inner cylindrical space, and the piercing projections protrude outside the cylinder portion from the support portion.

6. The microneedle of claim 2, wherein the target shape has a center of gravity in the target area surrounded by the straight lines connecting the adjacent surface-defining structures in the outer peripheral region, and the plurality of piercing projections includes a piercing projection positioned at a vertex of the target shape.

7. The microneedle of claim 2, wherein the plurality of surface-defining structures includes a surface-defining projection having a shape which is different from shapes of other surface-defining structure in the outer peripheral region when viewed in the direction perpendicular to the first surface.

8. The microneedle of claim 2, wherein the plurality of surface-defining structures in the outer peripheral region is not evenly distributed in a circumferential direction of the substrate.

9. The microneedle of claim 1, wherein the plurality of surface-defining structures includes three to five surface-defining structures which are distributed across an entire outer peripheral region.

10. The microneedle of claim 9, wherein the three surface-defining structures are distributed across the entire outer peripheral region.

11. The microneedle of claim 9, wherein the surface-defining structures each have a length equal to one-quarter or less of a length of the piercing projections in a thickness direction of the substrate.

12. The microneedle of claim 11, wherein the surface-defining structures are the surface-defining projections formed such that each of the surface-defining projections has a length of 50 μm or more.

13. The microneedle of claim 9, wherein the target shape has a center of gravity in the target area surrounded by the straight lines connecting the adjacent surface-defining structures in the outer peripheral region, and the plurality of piercing projections includes a piercing projection positioned at a vertex of the target shape.

14. The microneedle of claim 9, wherein the plurality of surface-defining structures includes a surface-defining projection having a shape which is different from shapes of other surface-defining structure in the outer peripheral region when viewed in the direction perpendicular to the first surface.

15. The microneedle of claim 9, wherein the plurality of surface-defining structures in the outer peripheral region is not evenly distributed in a circumferential direction of the substrate.

16. The microneedle of claim 1, wherein the surface-defining structures each have a length equal to one-quarter or less of a length of the piercing projections in a thickness direction of the substrate.

17. The microneedle of claim 1, wherein the target shape has a center of gravity in the target area surrounded by the straight lines connecting the adjacent surface-defining structures in the outer peripheral region, and the plurality of piercing projections includes a piercing projection positioned at a vertex of the target shape.

18. The microneedle of claim 1, wherein the plurality of surface-defining structures includes a surface-defining projection having a shape which is different from shapes of other surface-defining structure in the outer peripheral region when viewed in the direction perpendicular to the first surface.

19. The microneedle of claim 1, wherein the plurality of surface-defining structures in the outer peripheral region is not evenly distributed in a circumferential direction of the substrate.

20. A microneedle assembly, comprising:
the microneedle of claim 1; and
an applicator having a cylinder portion that includes two opening ends and an inner cylindrical space between the opening ends,
wherein the substrate of the microneedle is housed in the inner cylindrical space, one of the two opening ends is a support portion having a shape which inwardly projects in a radial direction of the cylinder portion, three of the surface-defining sections included in the plane are in contact with the support portion in the inner cylindrical space, and the piercing projections protrude outside the cylinder portion from the support portion.

* * * * *